United States Patent [19]
Escano et al.

[11] Patent Number: 5,990,197
[45] Date of Patent: Nov. 23, 1999

[54] ORGANIC SOLVENT BASED INK FOR INVISIBLE MARKING/IDENTIFICATION

[75] Inventors: Nelson Zamora Escano; James John Krutak, Sr.; Max Allen Weaver, all of Kingsport, Tenn.

[73] Assignee: Eastman Chemical Company, Kingsport, Tenn.

[21] Appl. No.: 08/981,805

[22] PCT Filed: Oct. 27, 1997

[86] PCT No.: PCT/US97/19251

§ 371 Date: Jan. 5, 1998

§ 102(e) Date: Jan. 5, 1998

[87] PCT Pub. No.: WO98/18871

PCT Pub. Date: May 17, 1998

Related U.S. Application Data

[60] Provisional application No. 60/029,172, Oct. 28, 1996.

[51] Int. Cl.$^6$ .......................... C09D 11/02; C08G 63/16; C08G 63/20; C08K 3/30
[52] U.S. Cl. .......................... 523/160; 524/539; 528/282; 528/283; 528/289; 528/298; 106/31.15; 106/31.32; 106/31.64
[58] Field of Search .................................. 523/160, 161; 106/31.13, 31.14, 31.15, 31.32, 31.64; 524/539, 540; 528/289, 298, 282, 283

[56] References Cited

U.S. PATENT DOCUMENTS

| | | | |
|---|---|---|---|
| Re. 27,117 | 4/1971 | Byrne et al. | 260/314.5 |
| Re. 34,480 | 12/1993 | Eda | 540/139 |
| 3,630,941 | 12/1971 | Bergmark et al. | 252/186 |
| 3,734,874 | 5/1973 | Kibler et al. | 260/29.2 E |
| 3,779,993 | 12/1973 | Kibler et al. | 260/755 |
| 3,828,010 | 8/1974 | Davis et al. | 260/75 N |
| 4,202,491 | 5/1980 | Suzuki | 235/491 |
| 4,233,196 | 11/1980 | Sublett | 260/29.2 N |
| 4,250,078 | 2/1981 | McFarlane et al. | 260/40 R |
| 4,321,133 | 3/1982 | DiGiacomo | 209/3.3 |
| 4,335,220 | 6/1982 | Coney | 523/414 |
| 4,408,004 | 10/1983 | Pengilly | 524/398 |
| 4,420,581 | 12/1983 | McFarlane et al. | 524/431 |
| 4,423,814 | 1/1984 | White | 209/3.3 |
| 4,435,220 | 3/1984 | Watanabe et al. | 106/291 |
| 4,476,272 | 10/1984 | Pengilly | 524/398 |
| 4,535,118 | 8/1985 | Pengilly | 524/398 |
| 4,540,595 | 9/1985 | Acitelli et al. | 427/7 |
| 4,541,438 | 9/1985 | Parker et al. | 128/664 |
| 4,606,859 | 8/1986 | Duggan et al. | 540/122 |
| 4,649,064 | 3/1987 | Jones | 427/256 |
| 4,704,309 | 11/1987 | Coney et al. | 427/258 |
| 4,738,785 | 4/1988 | Langston et al. | 210/738 |
| 4,804,719 | 2/1989 | Weaver et al. | 525/420 |
| 4,816,386 | 3/1989 | Gotoh et al. | 430/495 |
| 4,824,948 | 4/1989 | Stark et al. | 540/125 |
| 4,883,714 | 11/1989 | Stockl et al. | 428/412 |
| 4,904,567 | 2/1990 | Maeda et al. | 430/270 |
| 4,910,292 | 3/1990 | Blount | 528/272 |
| 4,973,656 | 11/1990 | Blount | 528/272 |
| 4,975,220 | 12/1990 | Streitel et al. | 252/301.35 |
| 4,983,817 | 1/1991 | Dolash et al. | 235/462 |
| 4,992,204 | 2/1991 | Kluger et al. | 252/301.16 |
| 5,006,598 | 4/1991 | Adams et al. | 524/601 |
| 5,030,708 | 7/1991 | Krutak et al. | 528/272 |
| 5,055,500 | 10/1991 | Peters et al. | 523/319 |
| 5,093,147 | 3/1992 | Andrus et al. | 427/7 |
| 5,093,184 | 3/1992 | Edwards | 428/195 |
| 5,102,980 | 4/1992 | Krutak et al. | 528/272 |
| 5,110,968 | 5/1992 | Tai et al. | 556/415 |
| 5,120,610 | 6/1992 | Wegner et al. | 428/447 |
| 5,143,671 | 9/1992 | Peters et al. | 264/117 |
| 5,169,881 | 12/1992 | Peters et al. | 523/319 |
| 5,194,319 | 3/1993 | Onaka et al. | 428/224 |
| 5,201,921 | 4/1993 | Luttermann et al. | 8/506 |
| 5,208,630 | 5/1993 | Goodbrand et al. | 355/201 |
| 5,214,188 | 5/1993 | Tai et al. | 558/419 |
| 5,218,042 | 6/1993 | Kuo et al. | 524/601 |
| 5,260,052 | 11/1993 | Peters et al. | 424/63 |
| 5,292,855 | 3/1994 | Krutak et al. | 528/289 |

(List continued on next page.)

FOREIGN PATENT DOCUMENTS

| | | |
|---|---|---|
| 3-79683 | 4/1991 | Japan . |
| 1 537 375 | 12/1978 | United Kingdom . |
| 2 237 804 | 5/1991 | United Kingdom . |

OTHER PUBLICATIONS

Leach, R.H. and Pierce, R.J., The Printing Ink Manual, Blueprint, London (pp.218, 225–226, 234–236, 241, 245, 249–250), 1993.

Wheeler, Bob L., et al., "A Silicon Phthalocyanine and Silicon Naphthalocyanine: Synthesis, Electro–chemistry, and Electrogenerated Chemiluminescence", JACS, vol. 106, pp. 7404–7410 (1984).

Chemical Abstracts, vol. 77, p. 74, 141469m (1972).
Chemical Abstracts, vol. 106, p. 80, 86223s (1987).
Chemical Abstracts, vol. 114, p. 98, 230681z (1991).
Chemical Abstracts, vol. 114, p. 744, 196444n (1991).
Chemical Abstracts, vol. 114, p. 744, 196445p (1991).
Chemical Abstracts, vol. 114, p. 742, 196418g (1991).

*Primary Examiner*—Vasu Jagannathan
*Assistant Examiner*—Callie E. Shosho
*Attorney, Agent, or Firm*—Mark L. Davis; Bernard J. Graves, Jr.; Harry J. Gwinnell

[57] ABSTRACT

An organic solvent based polyester ink formulation having a fluorescing compound therein is suitable for ink jet printing applications. The ink is useful for producing invisible printing/markings on the surface of a variety of materials for identification, authentication, sorting, etc. Suitable printing substrates include porous and non-porous materials such as plastic, film, sheeting, fabric, paper, high gloss paper; metal, foils, plates; rubber; glass; cellophane; wood; and the like. The ink formulation contains at least one organic soluble polyester, having at least one near infrared fluorophore copolymerized therein, dissolved in an organic solvent. Suitable organic solvents include a $C_3$–$C_6$ carbon ketone, a $C_3$–$C_6$ carbon organic ester, a $C_1$–$C_3$ carbon alcohol, or a combination thereof. In a preferred embodiment, the polyester containing the copolymerized near infrared fluorophore is dissolved in a solvent comprising a $C_3$–$C_6$ carbon ketone and a $C_1$–$C_3$ carbon alcohol.

33 Claims, No Drawings

5,990,197
Page 2

U.S. PATENT DOCUMENTS

| | | | |
|---|---|---|---|
| 5,336,714 | 8/1994 | Krutak et al. | 524/608 |
| 5,397,819 | 3/1995 | Krutak et al. | 524/88 |
| 5,423,432 | 6/1995 | Krutak et al. | 209/577 |
| 5,461,136 | 10/1995 | Krutak et al. | 528/289 |
| 5,486,274 | 1/1996 | Thetford et al. | 204/157.5 |
| 5,525,516 | 6/1996 | Krutak et al. | 436/56 |
| 5,542,971 | 8/1996 | Auslander et al. | 106/21 |
| 5,553,714 | 9/1996 | Cushman et al. | 209/577 |
| 5,608,053 | 3/1997 | Thetford et al. | 540/140 |
| 5,614,008 | 3/1997 | Escano et al. | 523/161 |
| 5,665,151 | 9/1997 | Escano et al. | 106/31.15 |
| 5,702,511 | 12/1997 | De Saint-Romain et al. | 106/31.32 |
| 5,703,229 | 12/1997 | Krutak et al. | 540/140 |
| 5,755,860 | 5/1998 | Zhu | 106/31.15 |
| 5,766,324 | 6/1998 | Ikegaya et al. | 106/31.15 |

ORGANIC SOLVENT BASED INK FOR INVISIBLE MARKING/IDENTIFICATION

This application claims the benefit of U.S. Provisional Application No. 60/029,172 filed Oct. 28, 1996.

BACKGROUND

This invention relates to organic solvent based ink formulations suitable for ink jet printing by the piezoelectric impulse drop-on-demand (DOD) method and by using several available continuous ink jet printing systems, and which contain a suitable organic solvent and one or more polyesters having one or more copolymerized near infrared fluorophores dissolved therein.

It is desirable to provide intelligible markings that are virtually invisible to the human eye on the surface of articles for identification, authentication, sorting, etc. It is known to use near infrared fluorescent compounds which have minimal light absorption in the visible light wavelength range of about 400–700 manometers (nm) and which have strong light absorbance in the near infrared wavelength region of about 700–900 nm with accompanying fluorescence to produce fluorescent radiation having wavelengths longer than the wavelength of excitation (U.S. Pat. Nos. 5,093,147; 5,336,174; 5,423,432; 5,461,136).

Aqueous ink formulations for ink jet printing which contain at least one water-dissipatable sulfopolyester/amide containing near infrared fluorophore copolymerized therein have been reported in U.S. Pat. No. 5,614,008. These aqueous ink formulations are, unfortunately, only useful for printing onto porous cellulosic materials, such as, for example paper, wood, and the like. The aqueous formulations are slow to dry and are not suitable for printing on nonporous substrates, particularly glossy paper, glass, metal foils, metal sheeting, etc. The extended drying time may further result in the printed matter becoming smeared. Another disadvantage of the aqueous formulations is when these inks are printed on nonporous substrates, the printed markings do not sufficiently resist rubbing, scraping, scuffing, etc., to remain on the printed substrate. The disclosed sulfopolyester/amides containing copolymerized infrared fluorophores are not useful in formulating organic solvent base inks for ink jet printing because of their limited solubility in organic solvents.

U.S. Pat. No. 4,540,595 discloses a water-based ink which provides markings that fluoresce when exposed to light in the near infrared wavelength. The water-based ink is used to mark documents such as bank checks for automatic identification. The dyes used to make the ink are water-soluble, cationic phenoxazines (e.g. 3,7-bis(diethylamino) phenoxazonium nitrate is the preferred fluorescent material). These dyes are not invisible. They impart blue shades to the marked substrate and the inks are not suitable for printing on nonporous substrates. The dyes have limited solubility in organic solvents utilized in ink formulations.

U.S. Pat. No. 5,093,147 discloses infrared fluorescing inks which are useful for printing invisible markings on the surface of an article. The inks use known polymethine (cyanine) laser dyes. Although the dyes used provide invisible markings, the cyanine dyes, unfortunately, have the disadvantage of fading or decomposing upon brief exposure to ultraviolet light.

U.S. Pat. No. 3,630,941 discloses certain 16,17-dialkoxyviolanthrones (also called dibenzanthrones) to be useful as infrared fluorescent markers. However, they have a high molecular weight and at room temperature, have very limited solubility in solvents normally useful for preparing solvent based inks. These compounds also have significant absorption of light having wavelengths below 700 nm and, therefore, do not usually provide invisible markings.

Japanese Laid-Open Patent Application: Hei 3-79683 (Hanada, et al.) discloses ink formulations containing certain infrared absorbing naphthalocyanine compounds useful for printing bar codes and for identifying documents to prevent falsification and forgery. Various meltable waxes (e.g. Carnauba wax) and thermoplastic resins are used as vehicles in combination with alcohols and aromatic hydrocarbons to produce thermal transfer inks.

U.S. Pat. No. 5,336,714 discloses aqueous coating compositions containing about 20 weight percent to about 35 weight percent of a water-dissipatable sulfopolyester dispersed in about 65% to about 80% by weight of water. The sulfopolyester includes 0.1 ppm by weight to about 10% by weight of a thermally stable near infrared fluorophoric compound. The coating compositions are not suitable for ink jet printing because the compositions plug the orifices of the jets.

U.S. Pat. No. 5,461,136 discloses polyesters having certain infrared fluorophores copolymerized therein to provide an invisibly marked or tagged polymeric composition. The patent also discloses a method of detection for the copolymerized polyesters. However, the polymer compositions are not adequately dissolved in the solvents normally used for solvent based inks resulting in sludge or sediment upon standing.

There is a need to provide ink formulations for printing of intelligible near infrared fluorescent markings which overcome the problems inherent in the prior art. These ink formulations need to be printable by available ink printing methods, such as an ink jet printer, at commercial speeds on a variety of substrates. The inks need to be fast drying and to provide markings which are tough enough to resist scuffing, scraping, rubbing, etc. In particular the inks should be suitable for printing on substrates such as glossy paper, glass, metal, plastics, etc.

SUMMARY OF THE INVENTION

Briefly, the present invention provides for an ink having an organic solvent soluble polyester composition having a near infrared fluorophore copolymerized with the polyester. The ink further includes a binder selected from cellulose ester, condensed phenolic resin, polyketone, polyamide and polyurethane resin; an organic solvent soluble electrolyte; and an organic solvent selected from a $C_3$–$C_6$ aliphatic ketone, a $C_3$–$C_6$ aliphatic ester, a lower aliphatic alcohol or combinations thereof. The ink composition preferably can include a corrosion inhibitor as well as other constituents that permit proper ink fluidity under the desired conditions of use.

Another aspect of the invention provides for a method for detecting the fluorescent compound contained in the ink.

Surprisingly, inks made from polyesters which contain copolymerized near infrared fluorophores can be used to formulate solvent based inks. This is unexpected since when monomeric infrared fluorophores are used, such as those described in U.S. Pat. Nos. 5,336,714 and 5,461,136, and formulated into a solvent based ink, much of the absorption at the desired wavelength is lost. Although not wishing to be bound by any theory, it is believed that the apparent aggregation shifts the wavelength of maximum absorption of the aggregated dye significantly to lower wavelengths. Undesirably, the aggregated dye has greatly reduced fluorescent properties.

It is an object of the invention to provide an organic solvent based polyester composition having a near infrared fluorophore copolymerized therein.

It is another object of the invention to provide an organic solvent based polyester ink composition that is suitable for use in an ink jet printer.

It is another object of the invention to provide a method of detection and separation for articles having the organic solvent based polyester ink printer thereon.

These and other objects and advantages of the invention will become more readily apparent to those skilled in the art from the detailed description of the invention which follows.

DETAILED DESCRIPTION OF THE INVENTION

This invention provides solvent based inks for ink jet printing invisible markings on a variety of substrates, including those which are generally difficult to print upon.

Specifically the present invention relates to an ink composition comprising:

a. between about 1 and about 10 weight percent of at least one non-sulfo containing, organic solvent soluble polyester having from about 0.1 ppm by weight to about 10% by weight of a thermally stable near infrared fluorophore copolymerized therein;

b. between about 1 and about 5 weight percent of an organic solvent binder resin selected from a cellulose ester and/or condensed phenolic resin;

c. between about 0.01 and about 0.5 weight percent of a corrosion inhibitor;

d. between about 0.50 and about 1.0 weight percent of an organic solvent soluble electrolyte; and e. the remainder of said ink consisting of at least one $C_3$–$C_6$ aliphatic ketone, at least one $C_3$–$C_6$ aliphatic ester, or a combination thereof, with all of the weight percentages being based on the total weights of components a–e.

In another embodiment of the invention, the ink composition comprises:

a. between about 1 and about 10 weight percent of at least one non-sulfo containing, organic soluble polyester having from about 0.1 ppm by weight to about 10% by weight of a thermally stable near infrared fluorophore copolymerized therein;

b. between about 1 and about 5 weight percent of an organic solvent polymeric binder resin selected from the classes of condensed phenolic, polyketones, polyamides and polyurethanes;

c. between about 0.01 and about 0.5 weight percent of a corrosion inhibitor;

d. between about 0.50 and about 1.0 weight percent of an organic soluble electrolyte; and e. the remainder of said ink consisting of an organic solvent comprising at least 40 weight percent of at least one lower aliphatic alcohol and up to 60 weight percent of a $C_3$–$C_6$ aliphatic ketone or a $C_3$–$C_6$ aliphatic ester or mixture thereof, with all of the weight percentages in a–d being based on the total weights of components a–e.

The inks of the present invention have good storage stability and provide markings with adequate resistance to light fading (sunlight and fluorescent lights) and which are not easily removed by scuffing, scraping, rubbing, etc.

Methods for printing and detecting said inks are also included. The methods of detection are generally described in U.S. Pat. Nos. 5,336,714 and 5,461,136, the disclosures of which are incorporated herein by reference.

The inks of the present invention are particularly useful for printing invisible markings such as bar codes over backgrounds of white or colored material. Conventional black on white bar codes are useful only on areas of white or other light colored backgrounds. In contrast, the infrared fluorescent bar codes can be applied on a variety of colored surfaces, including even dark colors such as dark blue and black. Bar codes which fluoresce in the visible range when activated by ultraviolet light have the problem of interference from many dyes, pigments and UV absorbers which are normally used in dyeing and printing technology. Providing bar codes which fluoresce in the infrared region of the electromagnetic spectrum greatly reduces the problem of background interference.

The inks of this invention can be used for ink jet printing by the piezoelectric impulse drop-on-demand (DOD) method and by continuous ink jet systems such as the Scitex ink-jet imaging printer (Scitex Digital Printing, Inc., Dayton, Ohio 45420-4099); single nozzle, ink jet printers such as Amjet supplied by Domino Amjet, Inc. Gurnee, Ill. 60031 and Videojet printers supplied by Videojet Systems International, Inc., Wood Dale, Ill. 60191.

The non-sulfo containing organic solvent polyester containing the near infrared fluorophore is composed of:

i) 100 mole percent of monomer residues of at least one dicarboxylic acid selected from $C_6$–$C_{12}$ aliphatic dicarboxylic acids, 1,4-cyclohexane-dicarboxylic acid and $C_3$–$C_{12}$ oxa-aliphatic dicarboxylic acids which contain one or more oxygen atoms in the aliphatic chain and mixtures thereof;

ii) 100 mole percent of monomer residues of at least one diol selected from diethylene glycol, triethylene glycol, dipropylene glycol, tripropylene glycol, poly(ethylene glycols) having a number average molecular weight ranging from about 100 to about 10,000 and poly (propylene glycol) having a number average molecular weight ranging from about 200 to about 6,000; and iii) from about 0.10 ppm by weight to about 10%, by weight, of monomer residue of at least one copolymerized near infrared fluorophore containing at least one functional group which is reactive under polyester forming conditions, wherein the diacid residues and diol residues total 200 mole percent. The weight percent of monomer residue iii is based on the total weight of the polymer components (i), (ii) and (iii).

The organic solvent soluble linear polymers thus comprise polyesters having alternating residues of (1) one or more dicarboxylic acids and (2) one or more diols. The near infrared fluorophoric compounds can thus be incorporated into the polyester, so long as the near infrared fluorophoric compound has one, or preferably two, polyester reactive groups (e.g., hydroxy, carboxy, etc.) present.

The residues of component (i) may be derived from one or more dicarboxylic acids or their ester-forming derivatives such as dialkyl esters, bis(hydroxyalkyl) esters, or acid chlorides.

Examples of suitable poly(ethylene glycols) include relatively high molecular weight polyethylene glycols, some of which are available commercially under the designation CARBOWAX, a product of Union Carbide. Diethylene glycol is also especially suitable.

The term $C_6$–$C_{12}$ aliphatic dicarboxylic acid is used to describe straight or branched chain (preferably straight chain) aliphatic hydrocarbons containing two carboxy groups wherein the number of carbon atoms, include the carbons of the carboxy groups. The preferred aliphatic dicarboxylic acid is sebacic acid which contains 10 carbon atoms.

The term $C_3$–$C_{12}$ oxa-aliphatic dicarboxylic acid is used to describe aliphatic dicarboxylic acids which contain one or more oxygen atoms in the aliphatic chain, with typical monomers being represented by diglycolic acid (2,2'-oxodiacetic acid) and 3,6,9-trioxaundecanoic diacid (available from Hoechst Celanese Corp., Charlotte, N.C.).

The copolymerizable near infrared fluorophores are those disclosed in U.S. Pat. Nos. 5,461,136 and 5,423,432, and those compounds having reactive groups in U.S. Pat. No. 5,525,516, the disclosures of which are incorporated herein by reference. When low levels, e.g. from a few parts per million up to about 1,000 ppm, of the fluorophore are copolymerized into the polyester backbone the fluorophore may contain only one polyester reactive group and serve as a chain terminator and still provide an organic solvent soluble polyester. When higher levels of the copolymerized fluorophore in the polyester are desired, it is critical to the invention that the fluorophore contain at least two reactive functional groups. Although not to be bound by any theory, it is believed that the monofunctional monomer promote chain termination leading to a low molecular weight polyester. While multifunctional (greater than 2) lead to crosslinking causing a greater than desired molecular weight. Thus, the preferred infrared fluorophore monomers have two polyester reactive groups which allow incorporation of the fluorophore into the polyester chain.

Specifically, useful copolymerizable near infrared fluorophores include phthalocyanines, naphthalocyanines and squaraines (derivatives of squaric acid) and correspond to Formulae I, II and III:

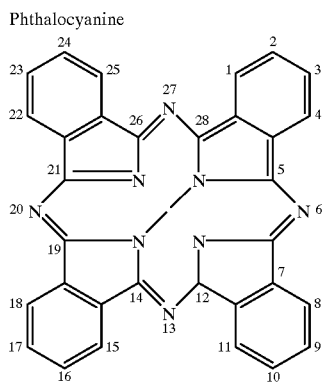

Phthalocyanine Ia

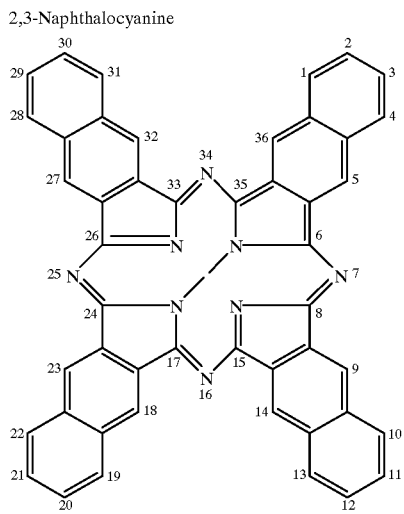

2,3-Naphthalocyanine IIa

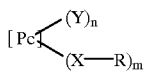

(I)

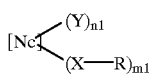

(II)

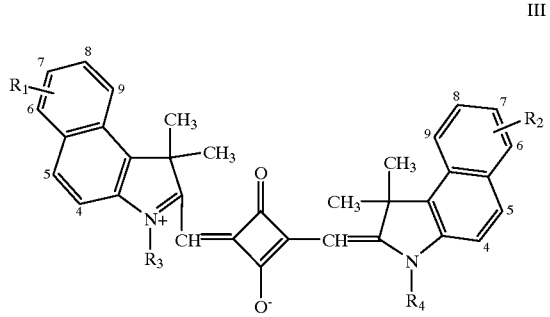

III wherein Pc and Nc represent the phthalocyanine and naphthalocyanine moieties of Formulae Ia and IIa, respectively, covalently bonded to hydrogen or to various metals, halometals, organometallic groups, and oxymetals including AlCl, AlBr, AlF, AlOH, $AlOR_5$, $AlSR_5$, Ca, Co, CrF, Cu, Fe, Ge, $Ge(OR_6)$, Ga, InCl, Mg, Mn, Ni, Pb, Pt, Pd, $SiCl_2$, $SiF_2$, $SnCl_2$, $Sn(OR_6)_2$, $Si(OR_6)_2$, $Sn(SR_6)_2$, $Si(SR_6)_2$, Sn, TiO, VO or Zn.

The $R_5$ and $R_6$ moieties are selected from hydrogen, alkyl, aryl, heteroaryl, lower alkanoyl, trifluoroacetyl, groups of the formulae:

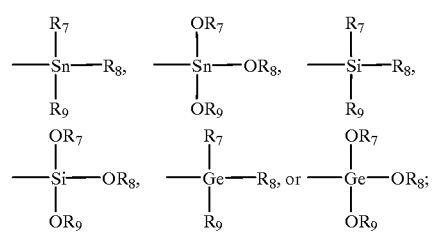

The $R_7$, $R_8$ and $R_9$ moieties are independently selected from alkyl, phenyl or phenyl substituted with lower alkyl, lower alkoxy or halogen.

The X moiety of formulae I and II is selected from oxygen, sulfur, selenium, tellurium or a group of the formula —N($R_{10}$)—, wherein $R_{10}$ is hydrogen, cycloalkyl, alkyl, acyl, lower alkylsulfonyl, or aryl. The moieties $R_{10}$ and R can be taken together to form an aliphatic or aromatic ring with the nitrogen atom to which they are attached.

The moiety Y is selected from alkyl, aryl, halogen or hydrogen.

The moiety R is selected from alkyl, alkenyl, alkynyl, cycloalkyl, aryl, heteroaryl,

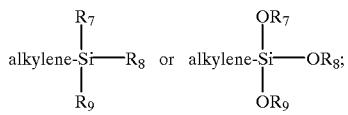

(X—R) moiety is alkylsulfonylamino, arylsulfonylamino, or a group selected from the formulae —X(C$_2$H$_4$O)$_z$R',

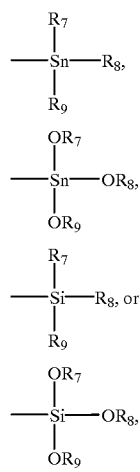

wherein R' is hydrogen or R as defined above and z is an integer of from 1–4. Further, two (X—R) groups can be taken together to form divalent substituents of the formula:

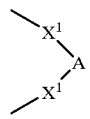

wherein each X$^1$ is independently selected from —O—, —S—, or —N(R$_{10}$)— and A is selected from ethylene; propylene; trimethylene; and such groups substituted with C$_1$–C$_4$ alkyl, C$_1$–C$_4$ alkoxy, aryl and cycloalkyl; 1,2-phenylene and 1,2-phenylene containing 1–3 substituents selected from C$_1$–C$_4$ alkyl, C$_1$–C$_4$ alkoxy or halogen.

The R$_1$ and R$_2$ moieties are independently selected from hydrogen, lower alkyl, lower alkoxy, halogen, aryloxy, lower alkylthio, arylthio, lower alkylsulfonyl; arylsulfonyl; lower alkylsulfonylamino, lower alkanoylamine, arylsulfonylamino, cycloalkylsulfonylamino, carboxy, unsubstituted and substituted carbamoyl and sulfamoyl, lower alkoxycarbonyl, hydroxy, lower alkanoyloxy,

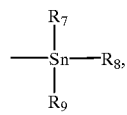

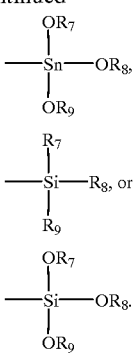

The R$_3$ and R$_4$ moieties are independently selected from hydrogen, lower alkyl, alkenyl or aryl; n is an integer from 0–16; n$_1$ is an integer from 0–24, m is an integer from 0–16; m$_1$ is an integer from 0–24; provided that the sums of n+m and n$_1$+m$_1$ are 16 and 24, respectively. It is to be understood that when n, m, n$_1$ or m$_1$ is 0, the respective moiety is absent.

Substituents (X—R) and (Y) are present in compounds Ia on the peripheral carbon atoms, i.e., in positions 1, 2, 3, 4, 8, 9, 10, 11, 15, 16, 17, 18, 22, 23, 24, 25 and substituents (X—R) and (Y) are present on the peripheral carbon atoms of IIa, i.e., in positions 1, 2, 3, 4, 5, 9, 10, 11, 12, 13, 14, 18, 19, 20, 21, 22, 23, 27, 28, 29, 30, 31, 32 and 36. Preferred (X—R) groups include those listed in Table 1 of U.S. Pat. No. 5,292,855 the disclosure of which is incorporated herein by reference.

In the above definitions, the term alkyl is used to designate a straight or branched chained hydrocarbon radical containing 1–12 carbons.

In the terms lower alkyl, lower alkoxy, lower alkyl-thio, lower alkoxycarbonyl, lower alkylsufonyl, lower alkylsufonylamino, lower alkanoylamino, lower alkanoyl and lower alkanoyloxy the alkyl portion of the groups contains 1–6 carbons and may contain a straight or branched chain.

The term "cycloalkyl" is used to represent a cyclic aliphatic hydrocarbon radical containing 3–8 carbons, preferably 5 to 7 carbons.

The alkyl and lower alkyl portions of the previously defined groups may contain as further substituents one or more groups selected from hydroxy, halogen, carboxy, cyano, C$_1$–C$_4$-alkoxy, aryl, C$_1$–C$_4$-alkylthio, arylthio, aryloxy, C$_1$–C$_4$-alkoxycarbonyl or C$_1$–C$_4$-alkanoyloxy.

The term "aryl" includes carbocyclic aromatic radicals containing 6–18 carbons, preferably phenyl and naphthyl, and such radicals substituted with one or more substituents selected from lower alkyl, lower alkoxy, halogen, lower alkylthio, N(lower alkyl)$_2$, trifluromethyl, carboxy, lower alkoxycarbonyl, hydroxy, lower alkanoylamino, lower alkylsulfonylamino, arylsulfonylamino, cycloalkylsulfonylamino, lower alkanoyloxy, cyano, phenyl, phenylthio and phenoxy.

The term "heteroaryl" is used to represent mono or bicyclic hetero aromatic radicals containing at least one "hetero" atom selected from oxygen, sulfur and nitrogen or a combination thereof. Examples of suitable heteroaryl groups include: thiazolyl, benzothiazolyl, pyrazolyl, pyrrolyl, thienyl, furyl, thiadiazolyl, oxadiazolyl, benzoxazolyl, benzimidazolyl, pyridyl, pyrimidinyl and triazolyl. These heteroaryl radicals may contain the same substituents listed above as possible substituents for the aryl radicals. The term triazolyl also includes structure IV and mixed isomers thereof,

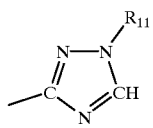

(IV)

wherein $R_{11}$ is hydrogen or selected from lower alkyl and lower alkyl substituted with one or two groups selected from hydroxy, halogen, carboxy, lower alkoxy, aryl, cyano, cycloalkyl, lower alkanoyloxy or lower alkoxycarbonyl.

The terms "alkenyl and alkynyl", are used to denote aliphatic hydrocarbon moiety having 3–8 carbons and containing at least one carbon-carbon double bond and one carbon-carbon triple bond, respectively.

The term halogen is used to include bromine, chlorine, fluorine and iodine.

The term "substituted carbamoyl" is used to denote a radical having the formula —$CONR_{12}R_{13}$, wherein $R_{12}$ and $R_{13}$ are selected from unsubstituted or substituted alkyl, alkenyl, alkynyl, cycloalkyl, aryl, or heteroaryl.

The term "substituted sulfamoyl" is used to denote a radical having the formula —$SO_2NR_{12}R_{13}$, wherein $R_{12}$ and $R_{13}$ are as defined above.

The term "alkylene" refers to a divalent $C_1$–$C_{12}$ aliphatic hydrocarbon moiety, either straight or branched-chain, and either unsubstituted or substituted with one or more groups selected from lower alkoxy, halogen, aryl, or aryloxy.

The term "acyl" refers to a group of the formula $R°C(O)$—O—, wherein $R°$ is preferably a $C_1$–$C_{10}$ alkyl moiety. The term "alkyl sulfonyl" refers to a group of the formula $R°SO_2$—, wherein $R°$ is as defined for acyl.

The term cellulose ester resin is used to include cellulose acetate butyrates (CAB) and cellulose acetate propionates (CAP) and includes CAB 381-0.1, CAB 381-0.5 and CAP 504-0.2 (all supplied by Eastman Chemical Company, Kingsport, Tenn.). The preferred cellulose ester resin is CAB 381-0.1.

The term condensed phenolic resin is used to describe a modified phenolic resin such as KRUMBHAAR® K-3107 as supplied by Lawter International, Inc. The term polyketone resin is used to describe ketone-based synthetic resins such as K-1717 HMP, K-1717-B and K-1717 supplied by Lawter International, Inc., Northbrook, Ill. The term polyamide resin is used to describe co-solvent polyamide resins such as POLYMID® 3370 as supplied by Lawter International, Inc. Northbrook, Ill. The term polyurethane resin is used to describe certain polymeric urethanes such as Thermoplastic Urethanes-150 Series (TPU-140), 150 Series (TPU-150) and 234 Series (TPU-234) as supplied by Morton Thiokol, Inc., Morton International, Inc., 100 North Riverside Plaza, Chicago, Ill.

The term $C_3$–$C_6$ aliphatic ketone is used to describe aliphatic ketones containing 3–6 carbon atoms such as acetone, methyl ethyl ketone, methyl propyl ketone, methyl isopropyl ketone, methyl butyl ketone, methyl isobutyl ketone, or mixture of these, etc., with methyl ethyl ketone (2-butanone) being the preferred ketone.

The term $C_3$–$C_6$ aliphatic ester is used to describe aliphatic esters containing 3–6 carbon atoms such as methyl acetate, ethyl acetate, methyl propionate, propyl acetate, isopropyl acetate, ethyl propionate, butyl acetate, isobutyl acetate, etc., or mixtures of these, with ethyl acetate being preferred.

The term lower aliphatic alcohol is used to include methanol, ethanol, n-propanol, isopropanol, ethylene glycol mono $C_1$–$C_4$ alkyl ethers and mixtures of these with ethanol being highly preferred.

Thus, this invention provides organic solvent soluble polyesters having copolymerized therein from about 0.1 ppm by weight to about 10% by weight, based on the final weight of the polymer, of a thermally stable, near infrared fluorescent compound. In a preferred embodiment, the solvent soluble polyesters have from about 1000 ppm to about 5%, by weight, and more preferably from about 100 ppm to about 2,000 ppm, based on the final weight of the polymer, of the near infrared fluorescent compound copolymerized therein.

In a preferred embodiment of the invention, corrosion inhibitors are added to the ink formulation to inhibit or reduce corrosion of metal parts, particularly the nozzles/orifices of the jet printer. Preferably, the corrosion inhibitors are selected from 1H-benzotriazoles, with 1H-benzotriazole being the most preferred corrosion inhibitor. The corrosion inhibitor 1H-benzotriazole is available from PMC Specialties, Cincinnati, Ohio under the trade name Cobratec 99.

Electrolytes are added to the ink formulations to provide conductivity. Typical organic solvent soluble electrolytes which can be used include the alkali metal salts of thiocyanic acid such as sodium and potassium thiocyanate and ammonium salts of sulfuric acid such as tetrabutylammonium hydrogen sulfate and tetrabutylammonium sulfate.

The functional groups which may be present on the near infrared fluorophore to allow incorporation into the polyester composition by covalent bonding include carboxy, hydroxy, or a carboxylate ester radical containing usually from about 2 to about 6 carbon atoms. The preferred ester is carbomethoxy.

It should be noted that the diacid component used in the polyester preparation may be replaced by a functional derivative such as the corresponding esters or acid chlorides when appropriate.

The polyesters are produced using typical polycondensation techniques well known in the art. For example, a mixture of one or more dicarboxylic acids, or ester forming derivatives thereof, and one or more diols may be heated in the presence of esterification and/or polyesterification catalysts at temperatures in the range of about 150° to about 300° C., and pressures of atmospheric to about 0.2 mm Hg. Normally, the dicarboxylic acid or derivative thereof is esterified or transesterified with the diol(s) at atmospheric pressure and at a temperature at the lower end of the specified range. Polycondensation then is effected by increasing the temperature and lowering the pressure while excess diol is removed from the mixture.

Typical catalyst or catalyst systems for polyester condensation are well-known in the art. For example, catalysts disclosed in U.S. Pat. Nos. 4,025,492; 4,136,089; 4,176,224; 4,238,593; and 4,028,527, incorporated herein by reference, are deemed suitable in this regard. Further, R. E. Wilfong, *Journal of Polymer Science*, 54 385 (1961) sets forth typical catalysts which are useful in polyester condensation reactions.

A preferred temperature range for a polyester condensation is about 260° C. to about 300° C.

The preparation of the useful near infrared fluorophores used in the practice of the invention is described in U.S. Pat. No. 5,461,136, the disclosure of which is incorporated herein by reference.

The inherent viscosities specified herein are determined at 25° C. using 0.5 g of polymer per 100 mL of a solvent consisting of 60 weight percent phenol and 40 weight percent tetrachloroethane. The weight average molecular weight (Mw) and number average molecular weight (Mn) values referred to herein are determined by gel permeation chromatography (gpc).

As a further aspect of the invention, there is provided a method for detecting an article having a near infrared fluorophore coated thereon. The method includes the steps of applying to at least one surface of the article the composition as described above; providing a means for producing an excitation light having a wavelength in the range of about 700 nanometers (nm) to about 2500 nm and exposing the composition to the excitation light whereby the fluorophoric composition produces a fluorescence; and detecting the fluorescence of the composition with a detection means.

One apparatus useful for practicing the method of the present invention is described in U.S. Pat. No. 5,292,855, the entire disclosure of which is incorporated herein by reference. Commercially available fluorometers are currently manufactured by SLM Aminco of Urbana, Ill.

The following Examples further illustrate the practice of the invention and are not to be considered as limiting the invention described herein.

EXAMPLE 1

A 300 mL :3-neck round-bottom flask was equipped with a magnetic stirrer, thermometer and gas inlet tube. Methanol (50 mL) was added followed by sodium metal (0.66 g, 0.029 mole) with stirring to facilitate reaction and solution, with a slow nitrogen purge applied. To this solution was added 12.54 g (0.058 mole) of 4-phenoxyphthalonitrile (A. W. Snow and J. R. Griffith, Macromolecules, 1984, 17, 1614–24), followed by additional methanol (50 mL). Anhydrous ammonia was bubbled in under the surface, giving an exotherm to 45° C. and total solution. The ammonia addition was continued until no more starting material was evident by thin-layer chromatography. The solution was clarified by filtering through a pad of Dicalite filter aid which had a small layer of charcoal on it and the filtrate was drowned into water. The oily product layer thus produced was washed by decantation with 500 mL portions of water (4–5 times or until pH reached about 7–8). After the final wash water was decanted off, methanol was added to dissolve the product, which crystallized upon stirring overnight at room temperature. After being collected by filtration, the greenish-yellow solid was washed with methylene chloride and dried in air. The yield was 13.75 g, 91.1% of the theoretical yield. Mass spectrometry showed the product to consist largely of the desired 5-phenoxy-1,3-diiminoisoindoline.

A mixture of 5-phenoxy-1,3-diiminoisoindoline (3.68 g, 0.016 m), 1,2,-3,4-tetrahydronaphthalene (20 mL) and tri-n-butylamine (10 mL) was stirred under a nitrogen sweep. Aluminum chloride (3.19 g, 0.024 m) was added to give a slurry. After the reaction mixture was heated at about 180° C. for 4 hours, it was allowed to cool to room temperature and diluted with methanol to enhance solubility to facilitate transfer into about 500 mL of ice-water mixture containing 10 mL HCl. The somewhat "greasy" solid product was collected by filtration and washed with dilute HCl. The filter cake was washed on the filter with cyclohexane and finally washed thoroughly with ethyl acetate and dried in air. Mass spectrometry indicated good quality 2(3), 9(10), 16(17), 23(24)-tetraphenoxy-Pc-Al-Cl (Pc=phthalocyanine moiety) having the desired molecular weight of 942 (1.56 g, 41.4% of the theoretical yield).

A reaction mixture of tetraphenoxy-chloroaluminum phthalocyanine (0.94 g), dimethyl-3-hydroxyisophtalate (0.24 g) and pyridine (20 g) was heated at reflux for 24 hours and allowed to cool to room temperature. Isopropanol (20 mL) was added and then precipitated, by the addition of water, the phthalocyanine product, which was collected by filtration, washed with water and dried in air (yield-0.90 g). In methylene chloride, absorption maxima were observed at 696 nm (104,585), 626 nm (32,882) and 343 nm (64,090) in the ultraviolet, visible and near infrared absorption spectra.

Components I–IV below were added to a 500 mL round bottom flask fitted with a vacuum outlet, stirrer, condensate take off and nitrogen inlet:

I. 78.44 grams (0.39 mole) sebacic acid;

II. 117.68 grams (0.59 mole) poly(ethylene glycol) (Mn-200);

III. 75 ppm Ti catalyst as titanium (IV) butoxide; and

IV. 0.14 grams ($1.25 \times 10^{-4}$ mole) of the infrared fluorescent compound (($C_6H_5O)_4PcAlOC_6H_3$-3,5-di—$CO_2CH_3$) (PC=phthalocyanine nucleus) produced above.

The flask and contents were immersed in a Belmont metal bath at 200° C. with a nitrogen sweep over the reaction mixture and held for 1.0 hour. The temperature was increased to 220° C., held for 2.0 hours, and then increased to 270° C. over about 10 minutes. Vacuum was applied to lower the pressure to about 0.1 torr over about 30 minutes and the polycondensation reaction completed by heating at a temperature of about 270° C. for 30 minutes. The resulting polymer which contains about 1000 ppm of infrared fluorophore had an inherent viscosity of 0.49 (measured in a 60/40 ratio by weight of phenol/ tetrachloroethane and at a concentration of 0.5 g per 100 mL). Using gel permeation chromatography, the polymer, had a weight average molecular weight of 21,1902, a molecular weight average of 8,182 and a polydispersity value of 2.68.

EXAMPLE 2

The polymeric product from Example 1 (140 g) was added to 2-butanone (300 g). The mixture was stirred at room temperature overnight (approx. 16 hrs). Solution of the polymer was complete. Additional 2-butanone was added while stirring to produce a solution which contained about 30.0 weight percent of the polymer in solution. The solution was diluted to a concentration of $7.68 \times 10^{-4}$ g/l with additional 2-butanone and exposed to 672 nm wavelength light from a laser diode source. Significant fluorescence with a maximum intensity at wavelength of approximately 676 nm was observed.

EXAMPLE 3

A mixture of aluminum phthalocyanine chloride (5.0 g, 0.0087 m), dimethyl 5-hydroxyisophthalate (1.83 g, 0.0087 m) and pyridine (25 mL) was heated and stirred at reflux for about 18 hours under nitrogen and then after cooling was drowned into water (500 mL). The green solid was collected by filtration, washed with water (1 l) and air dried. The product, $PcAlOC_6H_3$-3,5-di$CO_2CH_3$, had an absorption maximum at 675 nm (e-198,481) in the light absorption spectrum in N,N-dimethylformamide.

Example 1 was repeated except 0.14 grams ($1.87 \times 10^{-4}$ mole) of $PcAlOC_6H_3$-3,5-di$CO_2CH_3$ compound above was used as the near infrared fluorophore for copolymerization. This compound is described in greater detail in U.S. Pat. No. 5,461,136, the entire disclosure of which is incorporated herein by reference. The polymer which contained approximately 1,000 ppm of the near infrared fluorophore had an inherent viscosity of 0.49, a weight average molecular weight of 21,902, a number average molecular weight of 8,182 and a poly dispersity of 2.68.

EXAMPLE 4

The polymer of Example 3 (138 g) was added to 2-butanone (320 g) and the mixture stirred several hours at room temperature to achieve complete solution of the polymer (approx. 30% by weight). The solution was diluted to $7.68 \times 10^{-4}$ g/l with additional 2-butanone. The solution had fluorescence properties similar to the solution of Example 2.

EXAMPLE 5

Components I–IV below were added to a 500 mL round bottom flask fitted with a vacuum outlet, stirrer, condensate take off and nitrogen inlet:

I. 57.26 grams (0.28 moles) sebacic acid;

II. 158.24 grams (0.40 moles) poly(ethylene glycol) (Mn-400);

III. 75 ppm Ti catalyst as titanium (IV) butoxide; and

IV. 0.14 ($1.87 \times 10^{-4}$ mole) of the infrared fluorescent compound $PcAlOC_6H_3$-3,5-$diCO_2CH_3$ of Example 3 above.

The flask and contents were immersed in a Belmont metal bath at 200° C. with a nitrogen sweep over the reaction mixture and held for 1.0 hr. The temperature was increased to 220° C., held for 2.0 hrs, and then increased to 280° C. over about 10 minutes. Vacuum was applied to lower the pressure to about 0.10 torr over about 30 minutes and the polycondensation reaction completed by heating at about 280° C. for 60 minutes. The resulting polymer had an inherent viscosity of 0.21, a weight average molecular weight of 19,267, a number average molecular weight of 6,802 and a polydispersity of 2.83.

EXAMPLE 6

The polymer of Example 5 (192 g) was added to ethyl alcohol (448 g). The mixture was heated and stirred just below the boiling point until solution was complete. Additional ethyl alcohol was added to provide a solution which contained 30 weight percent of the polymer in ethyl alcohol.

EXAMPLE 7
Preparation of Ketone Based Ink for Ink Jet Printing

To produce an ink for invisible marking/ identification by ink jet printing, Components I–V below were mixed in a Cowles dissolver for about 1.0 hour using moderate shear.

| Component | Parts | |
|---|---|---|
| I | 21.50 | 2-butanone solution from Example 2 which contained about 30.0% by weight of polymer; |
| II | 13.00 | 2-butanone solution of CAB 381-0.1 cellulose acetate butyrate resin (Eastman Chemical Co.) - 30.0% by weight; |
| III | 0.05 | corrosion inhibitor (50% by weight solution of 1 (H)-benzotriazole (PMC Specialties) in propylene glycol); |
| IV | 0.70 | potassium thiocyanate; and |
| V | 64.75 | 2-butanone |
| | 100.00 | parts |

The composition thus produced was vacuum filtered in series through a depth filter (extra thick glass filter), Versapor 3000 (3µ), Versapor 1200 (1.2µ) and Versapor 800 (0.8µ) from Gelman Sciences. The ink thus produced had a viscosity of 4.0 centipoise, a pH of 8.65 and a conductivity of 1048 micro mhos. Using the Domino Codebox 2 Auto printer (Domino Amjet, Inc., Gurnee, Ill.), the ink was suitable for printing on porous and nonporous paper with no clogging at line speeds of about 100–500 feet per minute.

EXAMPLE 8
Preparation of Alcohol Based Ink for Ink Jet Printing

To produce an ink for invisible marking/ identification by ink jet printing, Components I–V below were mixed in a Cowles dissolver for about 1.0 hour using moderate shear.

| Component | Parts | |
|---|---|---|
| I | 21.70 | ethanol solution from Example 6 which contained about 30.0% by weight of polymer; |
| II | 38.00 | ethanol solution of K3107 rosin modified phenolic resin (Lawter Int., Inc.) - 40% by weight of resin in ethanol; |
| III | 0.05 | corrosion inhibitor (50% by weight solution of 1 (H)-benzotriazole PMC Specialties) in propylene glycol); |
| IV | 1.75 | potassium thiocyanate; |
| V | 8.00 | 2-butanone; and |
| VI | 30.50 | ethanol |
| | 100.00 | parts |

The composition this produced was vacuum filtered in series through a depth filter (extra thick glass filter), Versapor 3000 (3µ), Versapor 1200 (1.2µ) and Versapor 800 (0.8µ) from Gelman Sciences. The ink thus produced has a viscosity of 4.0 centipoise, a surface tension of 23.40 dynes/cm and a conductivity of 1355 micro mhos. Using the Domino Codebox 2 Auto printer (Domino Amjet, Inc., Gurnee, Ill.), the ink was suitable for jet printing bar codes on a variety of substrates including porous and glossy paper, cotton fabric, plastics (shaped articles, film and sheeting), metal foils, i.e., aluminum and tinfoil, metal sheeting, wood, glass and cellophane with no clogging and at line speeds of 100 to 500 feet per minute.

One skilled in the art will understand that various modifications can be made to the present invention without departing from the teachings hereof. It is to be further understood that the description of the preferred embodiments of the invention herein are not intended to limit the claims which define the scope of the invention.

We claim:

1. A composition of matter comprising:

a) from about 1 and about 10 weight percent of a non-sulfo containing, organic solvent soluble polyester having from about 0.1 ppm by weight to about 10% by weight of a thermally stable near infrared fluorophore copolymerized therein;

b) between about 1 and about 5 weight percent of a binder selected from a cellulose ester or a condensed phenolic resin;

c) between about 0.01 and about 0.5 weight percent of a corrosion inhibitor;

d) between about 0.50 and about 1.0 weight percent of an organic solvent soluble electrolyte; and e) the remainder of said composition having at least one $C_3$–$C_6$ aliphatic ketone, at least one $C_3$–$C_6$ aliphatic ester, or a combination thereof, wherein all weight percentages are based on the total weights of the constituents a–e.

2. The composition of claim 1 wherein said organic solvent soluble polyester comprises:

a) monomer residues of at least one dicarboxylic acid selected from the group consisting of $C_6$–$C_{12}$ aliphatic dicarboxylic acids, 1,4-cyclohexane-dicarboxylic acid, $C_3$–$C_{12}$ oxa-aliphatic dicarboxylic acids which contain one or more oxygen atoms in the aliphatic chain and mixtures thereof; and b) monomer residues of at least one diol selected from the group consisting of diethylene glycol, triethylene glycol, dipropylene glycol, tripropylene glycol, polyethylene glycols having number average molecular weights from about 100 to about 10,000 and polypropylene glycols having number average molecular weights of from about 200 to about 6,000.

3. The composition of claim 1 wherein said thermally stable near infrared fluorophore includes a monomer residue at least one functional group which is reactive under polyester forming conditions wherein said amount of said near infrared fluorophore copolymerized with said at least one organic solvent soluble polyester is based on the total weights of the organic solvent soluble polyester and near infrared fluorophore.

4. The composition of claim 3 wherein the amount of said near infrared fluorophore copolymerized with said polyester is from about 1,000 ppm by weight to about 5% by weight.

5. The composition of claim 3 wherein said near infrared fluorophores are selected from the group consisting of phthalocyanines, naphthalocyanines and squaraines corresponding to Formulae I, II and III:

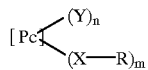 (I)

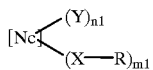 (II)

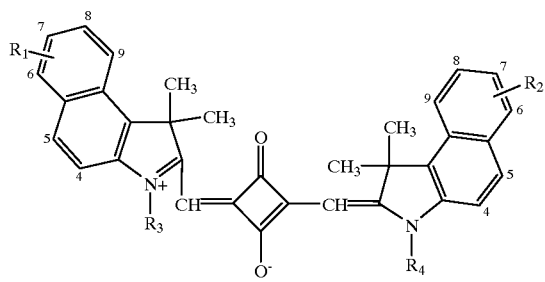 (III)

wherein Pc and Nc represent the phthalocyanine and naphthalocyanine moieties of Formulae Ia and IIa,

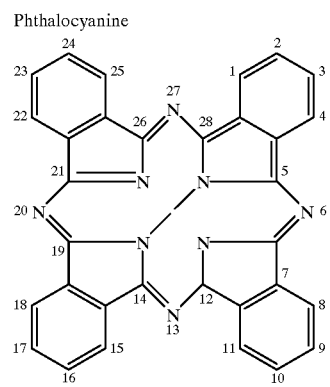 Ia

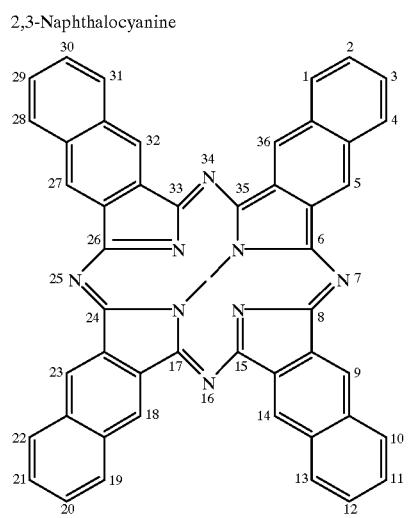 IIa respectively, covalently bonded to hydrogen or metals selected from the group consisting of AlCl, AlBr, AlF, AlOH, AlOR$_5$, AlSR$_5$, Ca, Co, CrF, Cu, Fe, Ge, Ge(OR$_6$), Ga, InCl, Mg, Mn, Ni, Pb, Pt, Pd, SiCl$_2$, SiF$_2$, SnCl$_2$, Sn(OR$_6$)$_2$, Si(OR$_6$)$_2$, Sn(SR$_6$)$_2$, Si(SR$_6$)$_2$, Sn, TiO, VO and Zn, wherein R$_5$ and R$_6$ are selected from the group consisting of hydrogen, alkyl, aryl, heteroaryl, lower alkanoyl, trifluoroacetyl, and groups of the formulae:

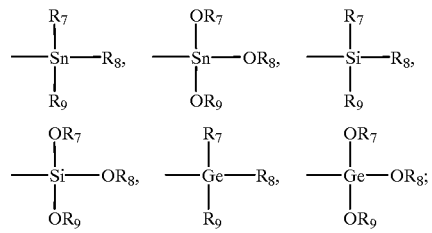

R$_7$, R$_8$ and R$_9$ are independently selected from alkyl, phenyl, phenyl substituted with lower alkyl, phenyl substituted with lower alkoxy or halogen;

X is selected from oxygen, sulfur, selenium, tellurium or a group of the formula —N($R_{10}$)—, wherein $R_{10}$ is selected from hydrogen, cycloalkyl, alkyl, acyl, lower alkylsulfonyl, or aryl or $R_{10}$ and R taken together form an aliphatic or aromatic ring with the nitrogen atom to which they are attached;

Y is selected from alkyl, aryl, halogen or hydrogen;

R is selected from alkyl, alkenyl, alkynyl, cycloalkyl, aryl, heteroaryl,

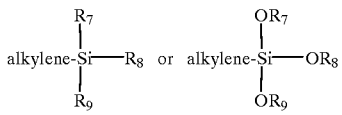

(X—R) is selected from alkylsulfonylamino, arylsulfonylamino, or a group selected from the formulae —X($C_2H_4O$)$_z$R',

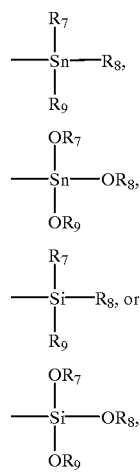

wherein R' is selected from hydrogen or R as defined above; z is an integer of from 1–4; or two (X—R) groups can be taken together to form divalent substituents of the formula

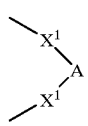

wherein each $X^1$ is independently selected from —O—, —S—, or —N($R_{10}$)— and A is selected from the group consisting of ethylene; propylene; trimethylene; and such groups substituted with $C_1$–$C_4$ alkyl, $C_1$–$C_4$ alkoxy, aryl and cycloalkyl; 1,2-phenylene and 1,2-phenylene containing 1–3 substituents selected from $C_1$–$C_4$ alkyl, $C_1$–$C_4$ alkoxy or halogen;

$R_1$ and $R_2$ are independently selected from the group consisting of hydrogen, lower alkyl, lower alkoxy, halogen, aryloxy, lower alkylthio, arylthio, lower alkylsulfonyl; arylsulfonyl; lower alkylsulfonylamino, lower alkanoylamino, arylsulfonylamino, cycloalkylsulfonylamino, carboxy, unsubstituted and substituted carbamoyl and sulfamoyl, lower alkoxycarbonyl, hydroxy, lower alkanoyloxy,

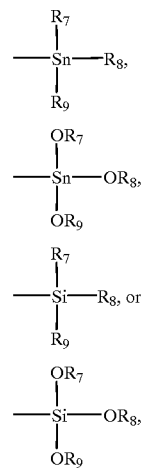

$R_3$ and $R_4$ are independently selected from hydrogen, lower alkyl, alkenyl or aryl; n is an integer from 0–16; $n_1$ is an integer from 0–24, m is an integer from 0–16; $m_1$ is an integer from 0–24; provided that the sums of n+m and $n_1$+$m_1$ are 16 and 24, respectively.

6. The composition of claim 5 wherein said near infrared fluorophore compound is a squaraine compound of Formula III, wherein $R_1$ and $R_2$ are independently carboxy, or lower alkoxycarbonyl.

7. The composition of claim 5 wherein said near infrared fluorophore compound is a 2,3-naphthalocyanine compound of Formula II, wherein Y is hydrogen, $n_1$ is 24 and $m_1$ is 0.

8. The composition of claim 5 wherein said near infrared fluorophore compound is a 2,3-naphthalocyanine compound of Formula II, wherein the naphthalocyanine moiety is bonded to $SiCl_2$, $(Si(OH)_2$, or $Si(OR_6)_2$.

9. The composition of claim 5 wherein said near infrared fluorophore compound is a phthalocyanine compound of Formula II, wherein X is oxygen or sulfur, R is aryl, Y is hydrogen, m is 4, and n is 12, and wherein the phthalocyanine moiety is bonded to AlCl, AlOH, $AlOCOCF_3$, $AlOR_5$, $SiCl_2$, $(Si(OH)_2$, or $Si(OR_6)_2$.

10. The composition of claim 1 wherein said near infrared fluorophore monomer includes two functional groups which are reactive under polyester forming conditions which allow copolymerization of said near infrared fluorophore into said at least one organic solvent soluble polyester.

11. The composition of claim 1 wherein said corrosion inhibitor is 1H-benzotriazole.

12. The composition of claim 1 wherein said electrolytes are selected from alkali metal salts of thiocyanic or ammonium salts of sulfuric acid.

13. The composition of claim 12 wherein said electrolytes are selected from sodium thiocyanate, potassium thiocyanate, tetrabutylammonium hydrogen sulfate or tetrabutylammonium sulfate.

14. An ink composition for use in an ink jet printer, said ink comprising
   a) from about 1 and about 10 weight percent of at least one organic solvent soluble polyester comprising:
      i) 100 mole percent of monomer residues of at least one dicarboxylic acid selected from $C_6$–$C_{12}$ aliphatic dicarboxylic acids, 1,4-cyclohexane-dicarboxylic acid and $C_3$–$C_{12}$ oxa-aliphatic dicarboxylic acids which contain one or more oxygen atoms in the aliphatic chain and mixtures thereof; and
      ii) 100 mole percent monomer residues of at least one diol selected from diethylene glycol, triethylene glycol, dipropylene glycol, tripropylene glycol, polyethylene glycols having number average molecular weights from about 100 to about 10,000 and polypropylene glycols having number average molecular weights of from about 200 to about 6,000, wherein said polyester has from about 0.1 ppm by weight to about 10% by weight of at least one thermally stable near infrared fluorophore copolymerized therein and the diacid residues and diol residues total 200 mole percent;

b) between about 1 and about 5 weight percent of a binder selected from a cellulose ester or a condensed phenolic resin;

c) between about 0.01 and about 0.5 weight percent of a corrosion inhibitor;

d) between about 0.50 and about 1.0 weight percent of an organic solvent soluble electrolyte; and e) the remainder of said composition consisting of at least one $C_4-C_6$ aliphatic ketone, at least one $C_4-C_6$ aliphatic ester, or a combination thereof, wherein all weight percentages are based on the total weights of the constituents a–e.

15. A method for detecting an article having a fluorescing ink printed thereon, said ink having detectable fluorescence when exposed to near infrared radiation, said method comprising the steps of:

a) applying to a surface of said article a fluorescing ink comprising:

i) from about 1 and about 10 weight percent of at least one non-sulfo containing, organic solvent soluble polyester having from about 0.1 ppm by weight to about 10% by weight of at least one thermally stable near infrared fluorophore copolymerized therein;

ii) between about 1 and about 5 weight percent of a binder selected from a cellulose ester or a condensed phenolic resin;

iii) between about 0.01 and about 0.5 weight percent of a corrosion inhibitor;

iv) between about 0.50 and about 1.0 weight percent of an organic solvent soluble electrolyte; and v) the remainder of said composition consisting of at least one $C_3-C_6$ aliphatic ketone, at least one $C_3-C_6$ aliphatic ester, or a combination thereof, wherein all weight percentages are based on the total weights of the constituents (i)–(v);

b) using an excitation means to subject said fluoresceing ink to an excitation radiation whereby said fluoresceing ink produces a detectable fluorescence; and c) using a detection means to detect said detectable fluorescence.

16. The method of claim 15 wherein said article has porous surface characteristics.

17. The method of claim 15 wherein said article has non-porous surface characteristics.

18. A composition of matter comprising:

a. between about 1 and about 10 weight percent of at least one non-sulfo containing, organic soluble polyester having from about 0.1 ppm by weight to about 10% by weight of at least one thermally stable near infrared fluorophore copolymerized therein;

b. between about 1 and about 5 weight percent of an organic solvent polymeric binder resin selected from the group consisting of condensed phenolic, polyketones, polyamides and polyurethanes;

c. between about 0.01 and about 0.5 weight percent of a corrosion inhibitor;

d. between about 0.50 and about 1.0 weight percent of an organic soluble electrolyte; and e. the remainder of said ink consisting of an organic solvent comprising at least 40 weight percent of at least one lower aliphatic alcohol and up to 60 weight percent of at least one compound selected from the group consisting of a $C_3-C_6$ aliphatic ketone, a $C_3-C_6$ aliphatic ester and mixtures thereof, with all of the weight percentages in a–d being based on the total weights of components a–e.

19. The composition of claim 18 wherein said organic solvent soluble polyester comprises:

a) 100 mole percent of monomer residues of at least one dicarboxylic acid selected from the group consisting of $C_6-C_{12}$ aliphatic dicarboxylic acids, 1,4-cyclohexanedicarboxylic acid, $C_3-C_{12}$ oxa-aliphatic dicarboxylic acids which contain one or more oxygen atoms in the aliphatic chain and mixtures thereof; and b) 100 mole percent monomer residues of at least one diol selected from the group consisting of diethylene glycol, triethylene glycol, dipropylene glycol, tripropylene glycol, polyethylene glycols having number average molecular weights from about 100 to about 10,000 and polypropylene glycols having number average molecular weights of from about 200 to about 6,000, wherein said polyester has from about 0.1 ppm by weight to about 10% by weight of at least one thermally stable near infrared fluorophore copolymerized therein and the diacid residues and diol residues total 200 mole percent.

20. The composition of claim 19 wherein said thermally stable near infrared fluorophore includes a monomer residue at least one functional group which is reactive under polyester forming conditions wherein said amount of said near infrared fluorophore copolymerized with said at least one organic solvent soluble polyester is based on the total weights of the organic solvent soluble polyester and near infrared fluorophore.

21. The composition of claim 20 wherein the amount of said near infrared fluorophore copolymerized with said polyester is from about 1,000 ppm by weight to about 5% by weight.

22. The composition of claim 21 wherein said near infrared fluorophore monomer includes two functional groups which are reactive under polyester forming conditions which allow copolymerization of said near infrared fluorophore into said at least one organic solvent soluble polyester.

23. The composition of claim 18 wherein said near infrared fluorophores are selected from the group consisting of phthalocyanines, naphthalocyanines and squaraines corresponding to Formulae I, II and III:

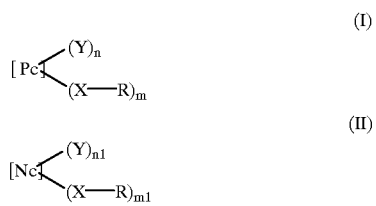

-continued (III)

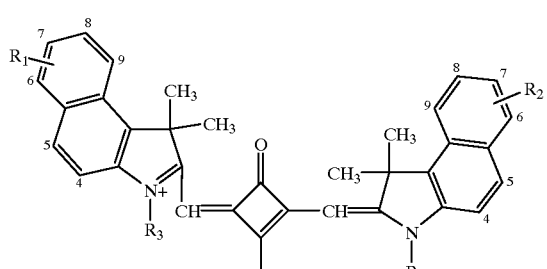

wherein Pc and Nc represent the phthalocyanine and naphthalocyanine moieties of Formulae Ia and IIa, Phthalocyanine                                                    Ia

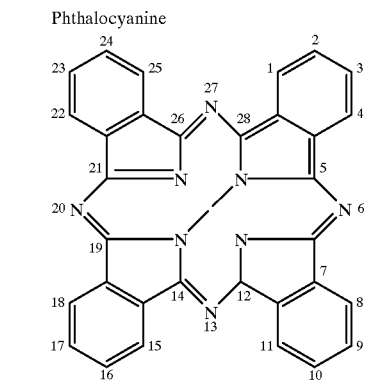

2,3-Naphthalocyanine                                             IIa

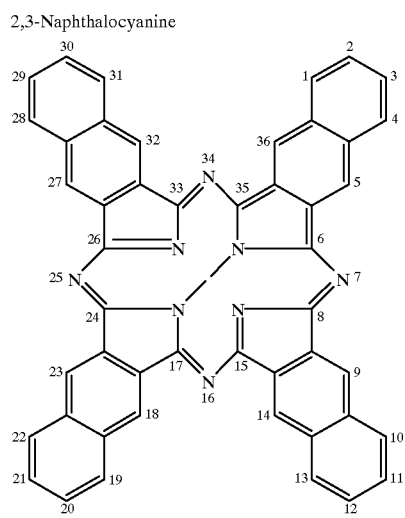

respectively, covalently bonded to hydrogen or metals selected from the group consisting of AlCl, AlBr, AlF, AlOH, AlOR$_5$, AlSR$_5$, Ca, Co, CrF, Cu, Fe, Ge, Ge(OR$_6$), Ga, InCl, Mg, Mn, Ni, Pb, Pt, Pd, SiCl$_2$, SiF$_2$, SnCl$_2$, Sn(OR$_6$)$_2$, Si(OR$_6$)$_2$, Sn(SR$_6$)$_2$, Si(SR$_6$)$_2$, Sn, TiO, VO and Zn, wherein R$_5$ and R$_6$ are selected from the group consisting of hydrogen, alkyl, aryl, heteroaryl, lower alkanoyl, trifluoroacetyl, and groups of the formulae:

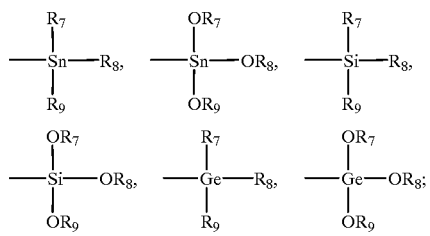

R$_7$, R$_8$ and R$_9$ are independently selected from alkyl, phenyl, phenyl substituted with lower alkyl, phenyl substituted with lower alkoxy or halogen;

X is selected from oxygen, sulfur, selenium, tellurium or a group of the formula —N(R$_{10}$)—, wherein R$_{10}$ is selected from hydrogen, cycloalkyl, alkyl, acyl, lower alkylsulfonyl, or aryl or R$_{10}$ and R taken together form an aliphatic or aromatic ring with the nitrogen atom to which they are attached;

Y is selected from alkyl, aryl, halogen or hydrogen;

R is selected from alkyl, alkenyl, alkynyl, cycloalkyl, aryl, heteroaryl,

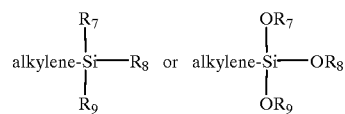

(X—R) is selected from alkylsulfonylamino, arylsulfonylamino, or a group selected from the formulae —X(C$_2$H$_4$O)$_z$R',

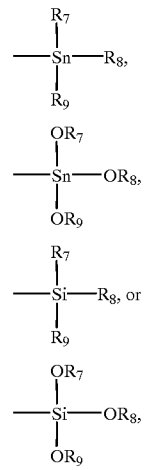

wherein R' is selected from hydrogen or R as defined above; z is an integer of from 1–4; or two (X—R) groups can be taken together to form divalent substituents of the formula

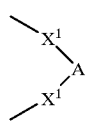

wherein each X$^1$ is independently selected from —O—, —S—, or —N(R$_{10}$)— and A is selected from the group consisting of ethylene; propylene; trimethylene; and such groups substituted with $C_1$–$C_4$ alkyl, $C_1$–$C_4$ alkoxy, aryl and cycloalkyl; 1,2-phenylene and 1,2-phenylene containing 1–3 substituents selected from $C_1$–$C_4$ alkyl, $C_1$–$C_4$ alkoxy or halogen;

$R_1$ and $R_2$ are independently selected from the group consisting of hydrogen, lower alkyl, lower alkoxy, halogen, aryloxy, lower alkylthio, arylthio, lower alkylsulfonyl; arylsulfonyl; lower alkylsulfonylamino, lower alkanoylamino, arylsulfonylamino, cycloalkylsulfonylamino, carboxy, unsubstituted and substituted carbamoyl and sulfamoyl, lower alkoxycarbonyl, hydroxy, lower alkanoyloxy,

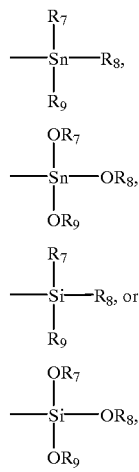

$R_3$ and $R_4$ are independently selected from hydrogen, lower alkyl, alkenyl or aryl; n is an integer from 0–16; $n_1$ is an integer from 0–24, m is an integer from 0–16; $m_1$ is an integer from 0–24; provided that the sums of n+m and $n_1$+$m_1$ are 16 and 24, respectively.

24. The composition of claim 23 wherein said near infrared fluorophore compound is a squaraine compound of Formula III, wherein $R_1$ and $R_2$ are independently carboxy, or lower alkoxycarbonyl.

25. The composition of claim 23 wherein said near infrared fluorophore compound is a 2,3-naphthalocyanine compound of Formula II, wherein Y is hydrogen, $n_1$ is 24 and $m_1$ is 0.

26. The composition of claim 23 wherein said near infrared fluorophore compound is a 2,3-naphthalocyanine compound of Formula II, wherein the naphthalocyanine moiety is bonded to $SiCl_2$, $Si(OH)_2$, or $Si(OR_6)_2$.

27. The composition of claim 23 wherein said near infrared fluorophore compound is a phthalocyanine compound of Formula II, wherein X is oxygen or sulfur, R is aryl, Y is hydrogen, m is 4, and n is 12, and wherein the phthalocyanine moiety is bonded to AlCl, AlOH, $AlOCOCF_3$, $AlOR_5$, $SiCl_2$, $Si(OH)_2$, or $Si(OR_6)_2$.

28. The composition of claim 18 wherein said corrosion inhibitor is 1H-benzotriazole.

29. The composition of claim 18 wherein said electrolytes are selected from alkali metal salts of thiocyanic or ammonium salts of sulfuric acid.

30. The composition of claim 29 wherein said electrolytes are selected from sodium thiocyanate, potassium thiocyanate, tetrabutylammonium hydrogen sulfate or tetrabutylammonium sulfate.

31. A method for detecting an article having a fluorescing ink printed thereon, said ink having detectable fluorescence when exposed to near infrared radiation, said method comprising the steps of:

a) applying to a surface of said article a fluorescing ink comprising:

i) between about 1 and about 10 weight percent of at least one non-sulfo containing, organic soluble polyester having from about 0.1 ppm by weight to about 10% by weight of at least one thermally stable near infrared fluorophore copolymerized therein;

ii) between about 1 and about 5 weight percent of an organic solvent polymeric binder resin selected from the group consisting of condensed phenolic, polyketones, polyamides and polyurethanes;

iii) between about 0.01 and about 0.5 weight percent of a corrosion inhibitor;

iv) between about 0.50 and about 1.0 weight percent of an organic soluble electrolyte;

v) the remainder of said ink consisting of an organic solvent comprising at least 40 weight percent of at least one lower aliphatic alcohol and up to 60 weight percent of at least one compound selected from the group consisting of a $C_3$–$C_6$ aliphatic ketone, a $C_3$–$C_6$ aliphatic ester and mixtures thereof, with all of the weight percentages in a–d being based on the total weights of components a–e;

b) using an excitation means to subject said fluresceing ink to an excitation radiation whereby said fluorescing ink produces a detectable fluorescence; and c) using a detection means to detect said detectable fluorescence.

32. The method of claim 31 wherein said article has porous surface characteristics.

33. The method of claim 31 wherein said article has non-porous surface characteristics.

* * * * *